(12) United States Patent
Stonisch (10) Patent No.: US 8,376,745 B2
(45) Date of Patent: Feb. 19, 2013

(54) METHOD OF USING A DEMONSTRATION DENTAL TEMPLATE WITH DIGITAL REPRESENTATION FOR MODELING DENTAL RESTORATIONS

(76) Inventor: Mary Sue Stonisch, Grosse Pointe Woods, MI (US)

( * ) Notice: Subject to any disclaimer, the term of this patent is extended or adjusted under 35 U.S.C. 154(b) by 0 days.

(21) Appl. No.: 12/905,765

(22) Filed: Oct. 15, 2010

(65) Prior Publication Data

US 2011/0033815 A1 Feb. 10, 2011

Related U.S. Application Data

(63) Continuation-in-part of application No. 12/079,386, filed on Mar. 26, 2008, now Pat. No. 8,043,092, which is a continuation-in-part of application No. 11/226,113, filed on Sep. 14, 2005, now Pat. No. 7,520,747, which is a continuation-in-part of application No. 11/096,602, filed on Apr. 1, 2005, now abandoned.

(51) Int. Cl.
*A61C 5/00* (2006.01)

(52) U.S. Cl. ....................................................... 433/215

(58) Field of Classification Search ................. 433/167, 433/169, 215, 218, 219, 229
See application file for complete search history.

(56) References Cited

U.S. PATENT DOCUMENTS

| | | |
|---|---|---|
| 1,654,387 A | 12/1927 | Stenz |
| 2,169,719 A | 8/1939 | Bush |
| 2,789,353 A | 4/1957 | Biggs |
| 3,861,044 A * | 1/1975 | Swinson, Jr. ............... 433/218 |
| 4,015,332 A | 4/1977 | Manne |
| 4,226,593 A | 10/1980 | Cohen et al. |
| 4,247,287 A | 1/1981 | Gigante |
| 4,583,947 A | 4/1986 | Hazar |
| 4,678,435 A | 7/1987 | Long |
| 4,710,127 A | 12/1987 | Bellavia et al. |
| 4,778,386 A | 10/1988 | Spiry |
| 4,906,186 A | 3/1990 | France, Jr. |
| 5,378,737 A | 1/1995 | Jacobs et al. |
| 5,382,164 A * | 1/1995 | Stern .............................. 433/223 |
| 5,385,469 A | 1/1995 | Weissman |
| 5,458,489 A | 10/1995 | Tennyson |
| 5,547,381 A | 8/1996 | Nutting |
| 5,569,036 A | 10/1996 | Goldiner et al. |
| 5,639,235 A | 6/1997 | Lapointe et al. |
| 5,775,909 A | 7/1998 | Langer |
| 5,803,737 A | 9/1998 | Lyalin |
| 5,894,017 A | 4/1999 | Sagel et al. |
| 5,904,481 A | 5/1999 | Shima |
| 5,916,653 A | 6/1999 | Kunstadter et al. |

(Continued)

FOREIGN PATENT DOCUMENTS

| | | |
|---|---|---|
| DE | 199 19 376 A1 | 11/2000 |
| WO | WO 03/049569 A1 | 6/2003 |

(Continued)

OTHER PUBLICATIONS

Website Literature, Fake Teeth Styles in Harwear, website www.drbukk.com/bukkstyles.html., 7 pages, printed from website Dec. 20, 2004.

(Continued)

*Primary Examiner* — Ralph Lewis
(74) *Attorney, Agent, or Firm* — Reising Ethington P.C.

(57) ABSTRACT

A dental prosthesis or demonstration dental template (10) simulates the front surfaces of a patient's teeth and is positioned to overlay over a patient's natural teeth (40) to provide an indication of what a permanent restoration may look like once applied to the patient's teeth. Digital imagery of the demonstration dental template is taken to record the desired plane of occlusion and desired incisal length along the vertical plane.

9 Claims, 6 Drawing Sheets

U.S. PATENT DOCUMENTS

| | | | |
|---|---|---|---|
| 5,927,984 | A | 7/1999 | Lin |
| 5,951,291 | A | 9/1999 | Albert et al. |
| 6,063,830 | A | 5/2000 | Deguchi et al. |
| 6,068,481 | A | 5/2000 | Worthington |
| 6,398,550 | B1 | 6/2002 | Caritg |
| 6,422,864 | B1 | 7/2002 | Glatt |
| 6,447,296 | B2 | 9/2002 | Worthington |
| 6,820,623 | B2 | 11/2004 | Cook |
| 7,118,375 | B2 | 10/2006 | Durbin et al. |
| 7,128,572 | B2 | 10/2006 | Lauciello et al. |
| 7,153,131 | B2 | 12/2006 | Crohn |
| 7,175,427 | B2 | 2/2007 | Smith |
| 7,357,637 | B2 | 4/2008 | Liechtung |
| 7,520,747 | B2 | 4/2009 | Stonisch |
| 7,758,345 | B1 * | 7/2010 | Christensen ............ 433/214 |
| 7,854,611 | B2 * | 12/2010 | Yau et al. ............ 433/213 |
| 8,043,092 | B2 * | 10/2011 | Stonisch ............ 433/215 |
| 2001/0036618 | A1 | 11/2001 | Worthington |
| 2004/0166463 | A1 | 8/2004 | Wen et al. |
| 2004/0229185 | A1 | 11/2004 | Knopp |
| 2005/0014109 | A1 | 1/2005 | Lim |
| 2005/0042569 | A1 | 2/2005 | Phan et al. |
| 2005/0196728 | A1 | 9/2005 | Goldiner |
| 2005/0227204 | A1 | 10/2005 | Hauck |
| 2007/0059667 | A1 | 3/2007 | Lim |

FOREIGN PATENT DOCUMENTS

WO    WO 2008/131159    * 10/2008

OTHER PUBLICATIONS

Lava™—Chairside Oral Sanner C.O.S., Get Ready to Be Impressed, Brochure, 3M ESPE, Dental Products 3M Center, Building 275-2SE-03, St. Paul, MN 55144, 2 pages.

Cadent, iTero™, creating the perfect byte, Your Talent, Our Technology, the Perfect Fit, Card, 2 pages.

William P.D. Wynne, DDS, How to Establish the Proper Plane of Occlusion With No Reliable Landmarks, Dentistry Today.com, Aug. 2005, printed from website May 14, 2010, 4 pages.

International Search Report and Written Opinion for PCT/US06/35464, Filing Date: Sep. 12, 2006, Date of Mailing: Mar. 15, 2007, 9 pages.

* cited by examiner

METHOD OF USING A DEMONSTRATION DENTAL TEMPLATE WITH DIGITAL REPRESENTATION FOR MODELING DENTAL RESTORATIONS

RELATED APPLICATIONS

This application is a continuation-in-part of U.S. Ser. No. 12/079,386 filed on Mar. 26, 2008 which is a continuation-in-part of U.S. Ser. No. 11/226,113 filed on Sep. 14, 2005 now U.S. Pat. No. 7,520,747 B2 issued on Apr. 21, 2009, which is a continuation-in-part of abandoned U.S. Ser. No. 11/096,602 filed on Apr. 1, 2005.

TECHNICAL FIELD

The field of this invention relates to demonstration dental templates and a method for providing a visual representation to a dental patient of a potential restoration and digitization of the demonstration dental template to provide horizontal plane of occlusion and length of teeth information for manufacturing and/or placing dental restorations.

BACKGROUND OF THE DISCLOSURE

Human beings are a social animal and a person's face communicates important information to other people. A smile is a very important part of human communication and socialization. A genuine broad smile can help a person fit in and makes others who see the smile comfortable and even happy.

Teeth are an important part of a person's smile. Unattractive teeth or defects in a person's teeth can detract from the overall appearance of the face particularly when a person smiles. Dentists have long improved defective teeth with a permanent dental overlay (often referred to as a "permanent overlay" or "porcelain overlay" because they are usually made from plastic or porcelain, and are usually a veneer, crown, bridge, implant or other restoration generally all hereinafter referred to as a "prosthesis or "restoration") to enlarge, straighten, brighten, or fill in breaks or gaps in a person's teeth. These restorations may be made from a variety of materials for example, plastics, resins, porcelains, lithium disilicate, or porcelain fused to metal. A person who has excessively small teeth in part due to excessive gums can enlarge the teeth by re-contouring the gum line with the removal of some gum tissue sometimes in conjunction with a new restoration. People with yellow teeth or dark stains in their teeth can brighten their smile with a brighter whiter restoration.

As important as a smile is, many people with serious and unsightly defects in their smile decline to have a restoration to improve the smile for various reasons. One of these reasons is that a person may not be willing to undergo a permanent and irreversible treatment unless there is a high assurance in the person's mind that the procedure will greatly enhance his/her smile and the installed restoration will be comfortable in the mouth against his/her natural teeth. The person may not have the vision or knowledge as to how such a restoration can improve his/her smile. A person may initially resist the incorporation of dental prosthesis by being under the impression that the prosthesis may be uncomfortable in the mouth. Dentists until now had no easy method to demonstrate how such a restoration can improve the smile or to counteract the fears of discomfort. As a consequence of this lack of knowledge and information, only a limited amount of potential consumers accept and undergo a restoration procedure even though this dental treatment could greatly benefit a vastly wider consumer group.

A patient may not be willing to accept a permanent restoration until he/she is fully assured with the knowledge that the restoration is right for him/her and will produce some dramatic and known result. The patient needs to see a visual image of his/her own face and smile in a dynamic setting in a more three dimensional demonstration in order to obtain the needed assurance to accept the permanent restoration.

Recently, efforts have been made to visually demonstrate to the patient how a restoration may improve his/her smile. One such attempt is to take a photograph of a person smiling and then digitally alter the teeth to produce the desired smile improvement. While the digitization can produce a number of different looks by digitally altering the teeth in a variety of ways, this process is less than optimal. The result produces a somewhat static and two dimensional look to the patient. It also gives no knowledge to the consumer related to the comfort and feel of a prosthesis in the mouth.

Attempts have been made to place a temporary molded prosthesis or restoration of an individual tooth on a person's tooth. The prosthesis may adhere to the natural tooth for a short period of time in order to demonstrate to others the benefits and potential outcome of enhancing his/her teeth for a better smile. The temporary molded restoration is made from a moldable putty formed over a model of the desired smile changes. This putty is relined with an acrylic that is cured or glued onto a patient's teeth. A second approach is via direct sculpting composite on the surface of the patient's tooth and curing the composite in place once the desired shape has been sculpted. While these methods can provide the dynamic and three dimensional demonstration needed for the potential dental patient, they are time consuming costly procedures for fitting a plurality of teeth.

Once a patient decides to undergo cosmetic dentistry and obtain a restoration, the patient's teeth are prepared to receive the restoration. The restoration is then made often using a mold impression of the prepared teeth. Recently, digital systems have been commercially available that take digital photographs, videos or scans referred generally as digital imagery to provide a digitized three dimensional virtual visual model of the prepared teeth. The digital information can be downloaded into a CAD CAM machine on site for milling of a restoration in the dental office while the patient waits or the digital information can be electronically forwarded to a lab site for fabrication of model work and/or restoration. The three dimensional digital model contains the cast of the teeth along the tooth plane; however, the mold or three dimensional digital model often does not provide adequate information as to the vertical and horizontal inclinations and facial planes with respect to the tooth plane to provide the best location of the outer surface of the restoration. In dentistry, often the generally horizontal plane is referred to as the plane of occlusion or occlusal plane. Besides the cant of the generally horizontal plane of occlusion, the horizontal plane may be shifted along the vertical plane to generally determine the incisal length of the restorations. In the situation where there is only one, two or three tooth restorations to be fabricated, often the existing or adjacent teeth are used as a reference point to determine the desired positioning (horizontal and vertical planes) and lengths of restorations to be fabricated. However in the situation where there are more teeth involved in the restoration, additional information is needed to adequately determine the desired facial planes and cant of the restorations being fabricated.

Often, for best appearances sake, the overlay teeth need to be aligned with a facial plane that is angled with respect to the plane of occlusion of the natural teeth. In other words, the desired plane of occlusion often needs to be canted with respect to the original natural plane of occlusion. Due to the existing plane being canted with respect to the rest of the face, the top of the head, the forehead, the eyebrows, the eyes, cheekbones and the interpupillary plane for example, these generally horizontal planes that are visible are used to determine at which generally horizontal position should the restoration be located to determine a new smile line.

Dentists have in the past approximated the best angle by placing a stick, such as a cotton swab, into registration paste before it has set to indicate the best position along the vertical and horizontal planes of the overlay with respect to the tooth plane. This placement was done with no visual representation of human teeth and as such could only provide approximation to the ideal position. However with the advent of digital three dimensional virtual imaging, registration paste is being eliminated along with this method of recording the desired plane of occlusion.

Another obstacle for a patient is the time needed for the preparation of a temporary overlay to be used while the permanent overlay is being manufactured. Often the temporary is made using a poly-vinyl impression, commonly referred to as a wax impression, of the patient's original teeth. The teeth are then prepared for the restoration and the temporary is formed in place by using curing material. After the material is cured, it is then trimmed, polished and cemented or bonded in place. The problem with this procedure unless a desired wax up of the desired outcome has been completed, which adds time and expense to the case, is that the patient remains with a look substantially like original teeth. The patient desires to have the look of the new veneer, while the permanent restoration is being prepared as does the dentist to provide a more predictable outcome.

Temporary multi-tooth crown shells are known, but have only been applied to cuspid teeth and rearward for example the bicuspids and molars. Until now, there have been no full arched dental temporary that can also incorporate temporary crowns or temporary implants.

What is needed is a pre-fabricated, modifiable demonstration dental template that can quickly be adhered to patients' teeth to demonstrate the look of a permanent restoration for the patient. What is also needed is a dental prosthesis in the form of a demonstration dental template that provides the visual and tactile indicator to allow the consumer or patient to make a better educated decision prior to the onset of an aesthetic dental treatment; namely the application of a permanent restoration. What is also needed is a method of visually demonstrating how a dental prosthesis can improve his/her smile. Further, what is needed is a method to use the demonstration dental template also as a visual indicator to assist in determining the desired vertical and horizontal facial planes and tooth cants. The positioning along the vertical plane determines how long the tooth should be with respect to the lips and other facial features, i.e. the incisal length of the teeth. The overlay relative to the natural tooth plane can be set in a mold or a bite can be registered in paste of the overlay to communicate information of the desired vertical and horizontal facial planes for the restoration relative to the natural teeth with the laboratory to facilitate ideal end results with respect to facial planes and symmetry.

What is also needed is to create digital imagery of the demonstration dental template after it's installed in the patient to communicate the position information of the plane of occlusion and incisal length of the overlay in a digital format.

What is also needed is a full arched temporary pre-formed, modifiable shell including front incisors that can be easily relined as needed and applied to a patient's prepared teeth as a temporary while the permanent restoration are being manufactured. What is also needed is a temporary shell that matches in size, shape and color of the demonstration dental template that is used on the patient during the fabrication process of the final restoration so that the patient is not without a provisional. What is needed is a provisional that can be fabricated quickly, easily and economically. What is needed is a provisional that is modifiable in order to be able to add or subtract to it in order to mimic closely the desired outcome of both dentist and patient.

SUMMARY OF THE DISCLOSURE

In accordance with another aspect of the invention, a method for setting the vertical and horizontal planes of a dental prosthesis restoration includes preparing natural teeth for the installation of a permanent restoration. A demonstration dental template is positioned on the natural teeth at a desired vertical and horizontal facial planes such that the template appears vertical and horizontal relative to the vertical and horizontal facial planes for example with the top of head, forehead, eyebrows, eyes or cheekbones. The template is positioned and adhered at a desired vertical facial plane such that is pleasing to the eye, accepting of function, and that an appropriate amount of teeth is revealed on a smile.

In one embodiment, the demonstration dental template may be formed by a flat strip with a cervical edge having the shape of teeth at the gum line and the opposing incisal edge having the contour of incisal ends of the teeth crowns. The front side has shading to simulate individual teeth.

The strip may have its front side simulating the central incisors, lateral incisors, cuspids, first pre-molars, second pre-molars and first molars and may be cut to remove unneeded teeth for a demonstration. The strip may be pre-cut and peelable from a protective backing. The strip may have a pre-applied adhesive backing.

The method includes taking three dimensional digital imagery of the prepared natural teeth. The demonstration dental template is set in position to match the desired vertical and horizontal positions of the final restoration. Digital imagery is taken of the template to record its desired plane of occlusion and the desired incisal length of the teeth, i.e. to record the position of the vertical and horizontal facial planes of the template relative to the tooth plane of the natural teeth. The teeth are prepared and the method may include taking three dimensional digital imagery of the prepared natural teeth. Three dimensional digital imagery of the position template and of the prepared teeth can then be sent to the laboratory and used and correlated with each other to communicate desired vertical and horizontal of the restoration in making the restoration. The digital imagery of the template in the desired horizontal and vertical facial planes with the appropriate amount of tooth reveal can be a valuable tool prior to the onset of medical treatment and also once medical treatment has begun. The template can be scanned intraorally in both situations prior to tooth preparation in order to send digital imagery to the lab to begin diagnostic wax ups/medical treatment planning and then again after the teeth are prepared to confirm facial planes and tooth reveal.

Preferably, a temporary restoration has a front surface matching in size and shape to the front exposed surface of the demonstrating dental template constructed for use as a temporary restoration on the patient's prepared natural teeth. The temporary restoration preferably has its color matched to the color of the demonstration dental template. In one embodiment, the temporary restoration has a cavity for receiving the prepared teeth.

Preferably, a temporary veneer overlay for use over a patient's natural teeth prepared for fitting an overlay has a full curve to conform to the extrados arch of a patient's teeth and a front section simulating a plurality of incisors. Preferably, the temporary overlay has sections simulating cuspids and bicuspids on each side of the plurality of incisors simulations. Preferably the temporary overlay has sections simulating molars and a cavity for receiving the prepared teeth.

In accordance with one aspect of the invention, a method for setting a desired horizontal plane of occusion and the incisal length of a permanent restoration includes the steps of temporarily adhering a demonstration dental template at a desired position to overlay in front of the teeth of a patient at a desired plane of occusion and at a desired incisal length to provide an unobstructed view of the demonstration dental template to the patient. Digital imagery of the demonstration dental template at the desired position is taken to record the desired plane of occlusion and the desired incisal length. In addition, a bite registration taken on an incisal bite fork can aid in transferring this information to a jaw simulator prior to the beginning of any medical treatment for the purposes of planning the case. The demonstration dental template is removed from the natural teeth and the natural teeth are prepared for the installation of a permanent restoration. Three dimensional digital imagery of the prepared teeth is taken. The three dimensional digital imagery of the prepared teeth is correlated with the digital imagery of the demonstration dental template for use in analyzing the teeth and how they will function as well as in manufacturing the permanent restoration by allowing the information of horizontal and vertical planes and incisal reveal gathered through the use of the template to be transferred through digitization and used in fabrication of the final restoration for more predictable results.

Preferably, the step of adhering the demonstration dental template occurs before the steps of preparing of the natural teeth for the installation of the permanent restoration, i.e. the demonstration dental template is temporarily adhered to unprepared teeth.

Alternatively, the preparing of the natural teeth is before temporarily adhering the demonstration dental template, whereby the demonstration dental template is temporarily adhered to the natural teeth that are already prepared for a permanent restoration and the information regarding facial planes and tooth reveal can either be captured or confirmed and once again transferred to the lab by hand or digitization as a communication tool to aid in the fabrication of the final restoration.

BRIEF DESCRIPTION OF THE DRAWINGS

Reference now is made to the accompanying drawings in which.

DETAILED DESCRIPTION OF THE PREFERRED EMBODIMENT

Figure 1:
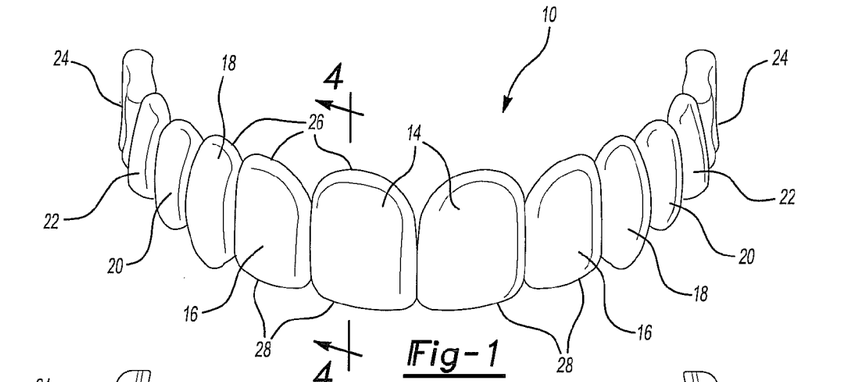
FIG. 1 is a perspective view of a demonstration dental template in accordance with one embodiment of the invention.
Figure 2:
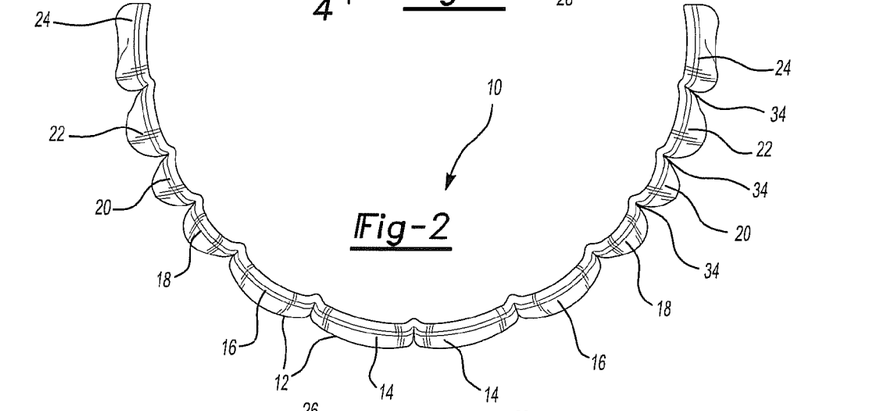
FIG. 2 is a top plan view of the demonstration dental template as shown in FIG. 1.

Referring now to FIG. 1, a demonstration dental template 10 is shown that simulates natural teeth of a patient. Demonstration dental template 10 is made from material like urethane, e.g. Santoprene™ material and is shaped to be positioned to abut against the front surface of a patient's natural teeth 40 shown in FIG. 5. Front surface 12 of the template has a finished porcelain look to simulate natural teeth. The front surface 12 is scalloped to mimic the natural division of individual teeth such as the front central incisors 14, lateral incisors 16, cuspids 18, first premolars 20, second premolars 22 and first molars 24.

Figure 3:
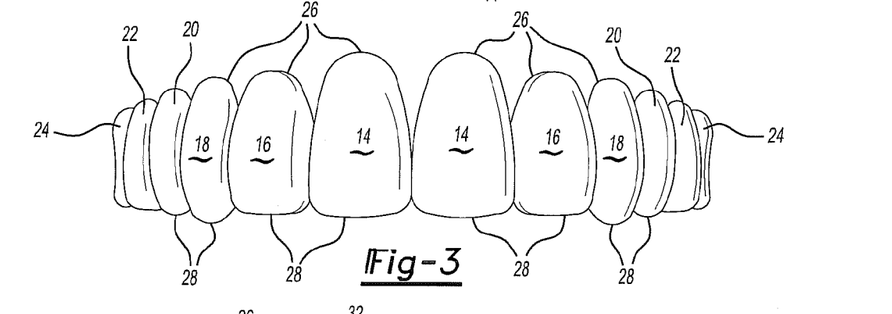
FIG. 3 is a front elevational view of the demonstration dental template as shown in FIG. 1.
Figure 4:
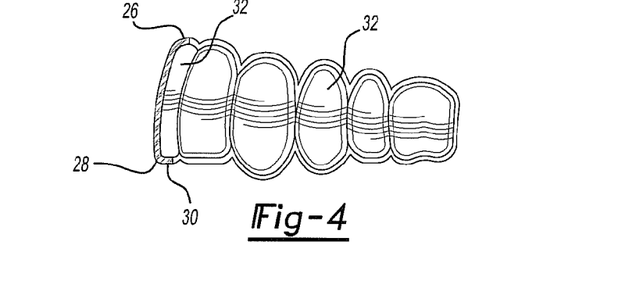
FIG. 4 is a cross-sectional view taken along lines 4-4 shown in FIG. 1.

Top edge 26 of the demonstration dental template 10 is contoured to simulate the top of natural teeth to define the gum line. The incisal bottom edge 28 of the demonstration dental template simulates the incisal (or biting) end of the upper teeth. The biting (incisal) edge 28 as shown more clearly in FIGS. 3 and 4 forms a lip or ledge 30 to rest on the existing biting edge. However, the template can be moved up or down to position the template with a degree of reveal that reflects the amount of tooth visible in the final restoration. The rear surface 32 is contoured with a generally flat-to-slightly concave negative shape to abut the individual natural teeth of the patient.

The urethane or Santoprene™ material allows the template to flex to match the extrados of the arch of the patient's natural teeth 40 and to abut against the patient's natural teeth 40. Other suitable flexible plastics or elastomeric materials with similar sanitary and flexible qualities can also be utilized in place of the urethane or Santoprene™. A temporary adhesive or glue for example a bite registration paste can be placed on the back surface 32 to retain the template in position against the patient's teeth 40 during inspection or examination. The adhesive may be pre-applied in a peel and stick format onto the template or may be applied in situ by the dentist or auxiliary personnel. The adhesive may be a thin coating and protected by a peel away protective layer.

Figure 5:
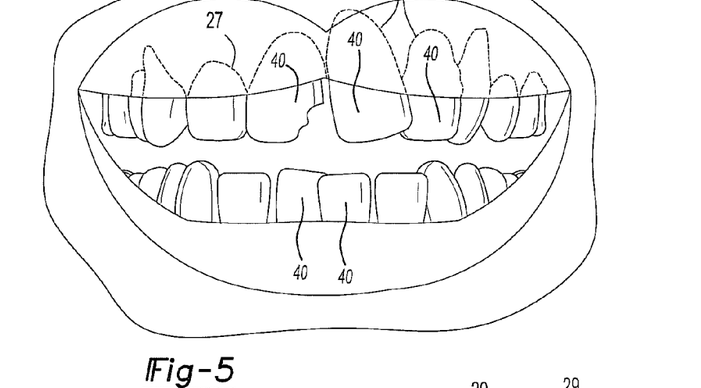
FIG. 5 is a front view of a patient's smile before use of the demonstration dental template.
Figures 6, 11:
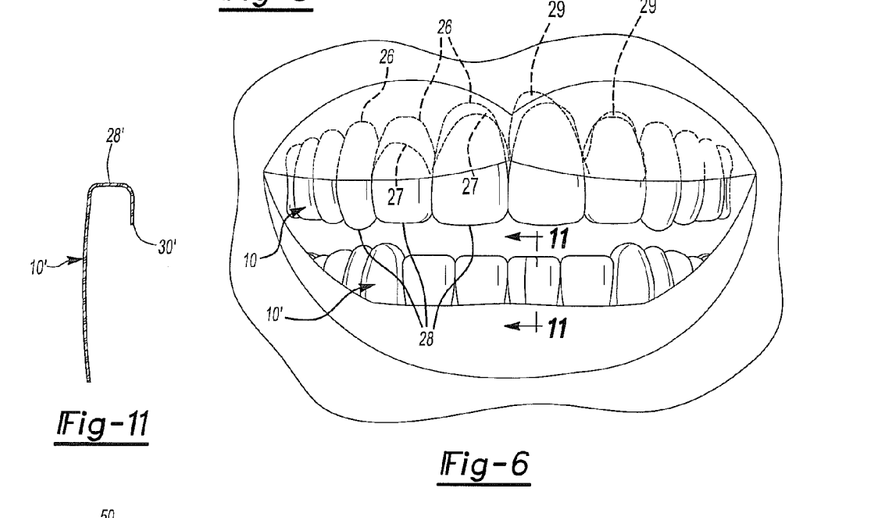
FIG. 6 is a front view demonstrating use of the demonstration dental template on a patient.
FIG. 11 is a cross-sectional view of the lower demonstration dental template taken along FIG. 11-11 shown in FIG. 6.
Figure 7:
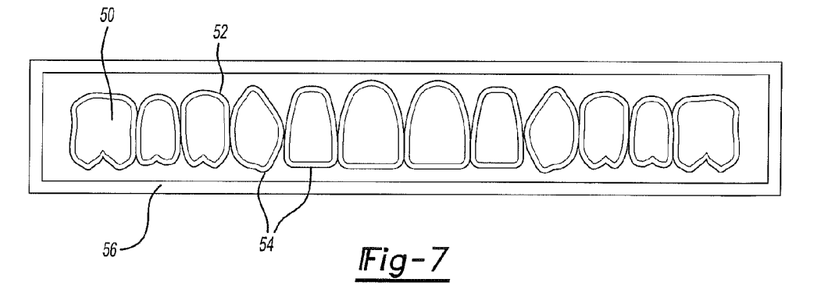
FIG. 7 is the front elevational view of an alternative embodiment disclosing the invention.
Figure 8:
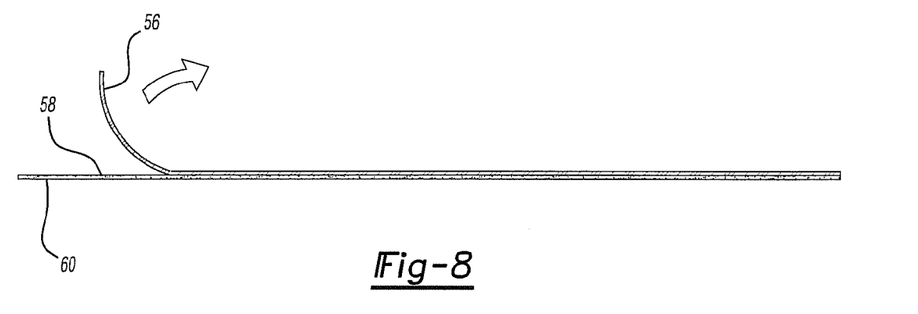
FIG. 8 is a top plan view of the embodiment shown in FIG. 7 showing the teeth peeled from its protective backing.
Figure 9:
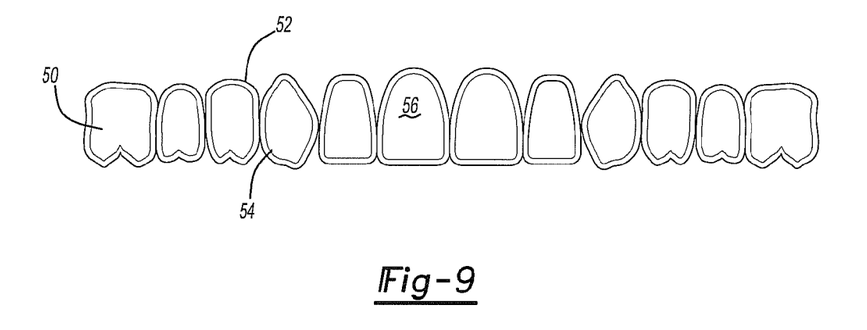
FIG. 9 is an elevational view of the embodiment shown in FIG. 7 with the single strip simulating teeth removed from the backing.

The dental patient or prospective dental patient can visually inspect the appearance of this demonstration dental template 10 in his mouth via a mirror. And can view the template from a variety of angles. In addition to the three dimensional visual aspect of the template the demonstration can provide indication of how a permanent porcelain restoration will feel against the front surface of his natural teeth and lips during different smiles, biting and lip motions. As shown in FIGS. 5 and 6 the patient and prospective patient can quickly see the difference between his natural teeth 40 and natural smile with a smile that includes a porcelain restoration by looking at template 10 in position. FIG. 5 illustrates natural teeth with misaligned and chipped teeth as well as asymmetrical gum heights or gum lines 27 and 29.

The method of demonstrating an improved smile to the patient becomes expeditious and time efficient. Providers such as a dentist, dental hygienist or other auxiliary personnel can merely place the template against the natural teeth of the patient. As shown in FIGS. 5 and 6, the template may extend over a low gum line 27 illustrates on the left side of FIG. 5 to the incisal edge (biting edge) end 28 of the crown at the lower edge above the patient's natural teeth with the flange 30 wrapped around or ending beyond the edge of the patient's natural teeth. This indicates to the dentist that some gum may be removed to raise the gum line. On the other hand, as shown on the right side of FIG. 6, if a high gum line 29 remains visible behind and above gum line 26 of the template, gum can be added back to lower the gum line 29 to create a symmetrical gum height as demonstrated by gum line 26 of the demonstration dental template 10. The template can be temporarily adhered to the teeth to allow the patient and prospective patient to inspect them dynamically in position. The patent can smile in a variety of ways and even talk while the template is in position. After inspection is over, the demonstration dental template 10 is merely removed from the patient's or prospective patient's mouth and his teeth. As an option, because of the ease of insertion and removal of the template, the patient can leave the office with the template to insert at home to show a spouse or loved one for reassurance and decision making. This allows the consumer and potential patient to make a better educated decision prior to the commencement of aesthetic dental procedures, namely the application of dental restorations.

Figure 13:
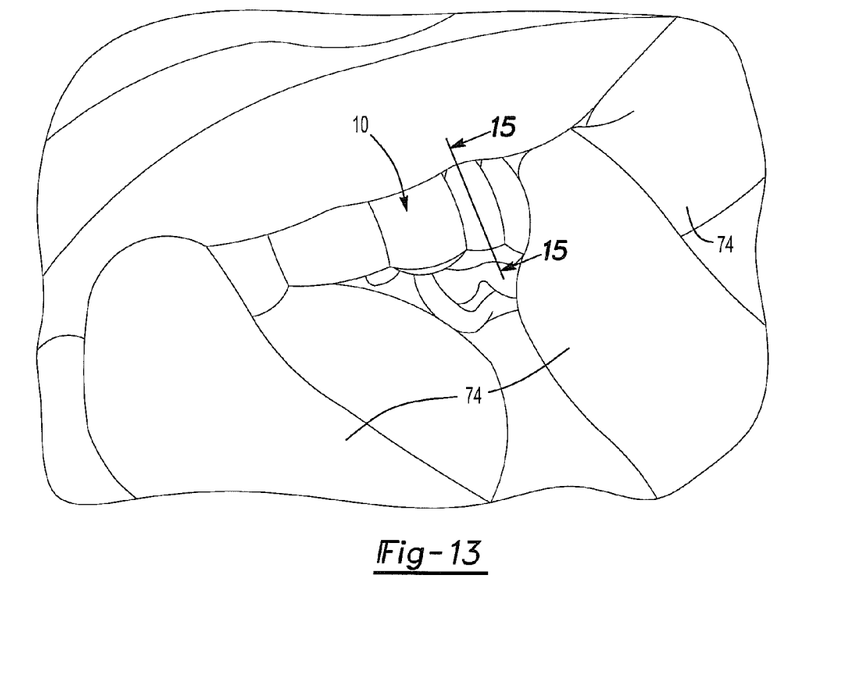
FIG. 13 is a perspective view of a dentist or auxiliary personnel adhering the demonstration dental template positioned onto and affixed to the prepared teeth.

The template can be manually maneuvered and placed in position by the dentist, technician or lay person as shown in FIG. 13. A mere grasping with a forefinger and thumb is often all that is needed to successfully place the template in position. Another installation device besides a hand is also foreseen to be used with this template.

Single and multiple combinations of shorter segments of the demonstration dental template can be used to illustrate smaller applications. In some instances, the first molars, second premolars, and first pre molars and possibly the cuspids may not be needed to improve patient's smile. In these cases, the demonstration dental template is cut at one of the defined interstices 34. For example, there may be instances, where the demonstration dental template has only the central incisors, lateral incisors, cuspids and first premolars. The rearward posterior teeth, i.e. the second premolars and first molars may be cut off the template 10 and discarded.

The removal of the template is also quick and easy. The temporary adhesive should be of a known type that provides a relatively weak securement so that a manual pull on the template will remove it from the natural teeth.

Figure 10:
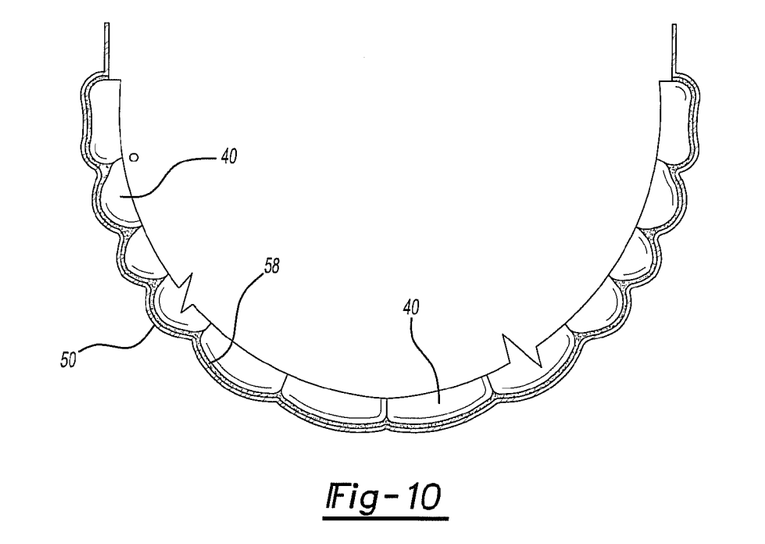
FIG. 10 is a top plan view of the alternative embodiment showing the strip in position against the natural teeth of a patient.

Another embodiment is shown in FIGS. 7-10. In the second embodiment, the demonstration dental template comprises a flat strip 50 that has contoured top and bottom edges 52 and 54. And the front surface 56 is photographed or shaded to simulate individual teeth and an adhesive backing 58 to adhere to the front teeth of the patient. The strip can be packaged flat and be peelable from a protective backing 60 that allows the adhesive backing to be easily peeled from the rear surface 58. The strip 50 is flexible to fit about the extrados of the arch of the natural teeth 40 and follow the general contour of each individual tooth 40 as shown in FIG. 10.

The demonstration dental templates may be prefabricated in various sizes, styles and shades to better fit and cosmetically blend with different sized mouths and varying types and shades of teeth. The use of the demonstration dental template on the front upper teeth may quickly give a visual and tactile indicator to allow the consumer and potential patient to make a better educated decision prior to the commencement of an aesthetic dental treatment namely the application of a permanent restoration.

Demonstration dental templates 10' as shown in FIGS. 6 and 11 are also foreseen to be used on occasion with lower teeth. If the template 10' is made for lower teeth, care needs to be directed to make the template 10' thin enough as with the permanent dental restoration so as not to interfere with the patient's bite. The lower dental template 10' would also have its incisal end 28' wrap further over the incisal end of the lower teeth to keep the edge 30' of the template hidden from normal viewing angles of the lower arch.

The temporary installation of the demonstration dental template is simple enough that any of the above described embodiments can also be disseminated to potential patients as a mail piece for installation by a lay person in order to intrigue the prospective patient. The use of the three dimensional or flat sticker embodiments may be used by dentists or dental laboratories to heighten consumer awareness and to instigate a prospective patient to make an appointment for a consultation to further investigate the feasibility of specific smile enhancement options through cosmetic surgery and traditional dental medical treatment.

Figure 12:
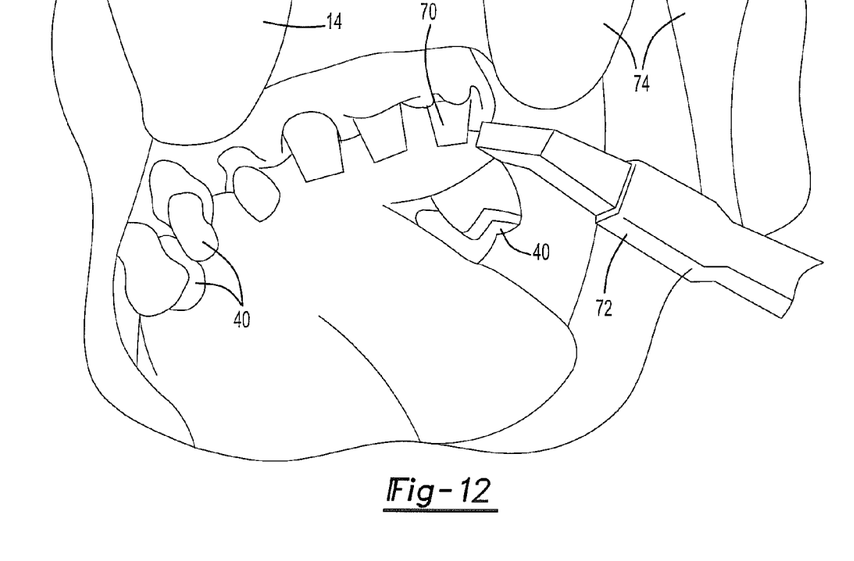
FIG. 12 is a view of taking three dimensional digital imagery of the prepared natural teeth.

The template can also be used to set the vertical, i.e. amount of reveal and horizontal planes of the restoration when a patient decides to proceed with the cosmetic restoration. Digital imagery of the dental demonstration template is taken as positioned in FIG. 6. The imagery is taken by an intraoral camera head 72 (as shown in FIG. 12). A three dimensional digital imaging system connected to the camera head 72 such as 1) Itero™ by Cadent Inc., 2) LAVA C.O.S. Scans by 3M ESPE or 3) Cerec™ is suitable. However, other three dimensional digital imaging systems adapted for dental use may be usable. This imagery is sent to the lab for manufacturing of a provisional restoration such as a provisional template.

Figure 14:
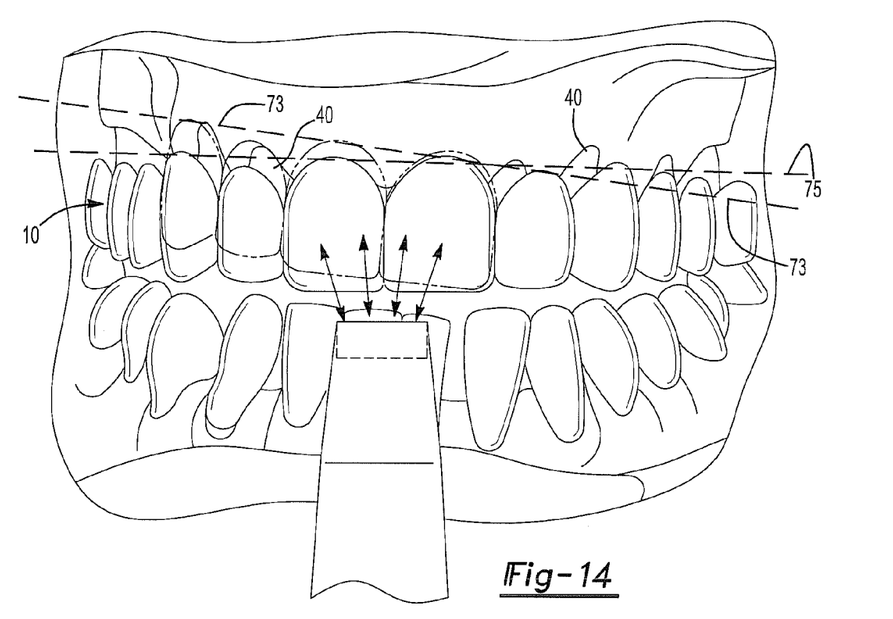
FIG. 14 is a partially schematic view illustrating a situation where the demonstration dental template is adhered to the desired position at desired vertical and horizontal facial planes and is canted with respect to the natural tooth plane due to a desire to change the tooth plane to mimic the facial planes as well as a desire to increase the visibility of the upper teeth by lowering them along the vertical plane and adding more reveal of a number of teeth and digital imagery is taken of the demonstration dental template.

The patient has the natural teeth shaped and prepared to receive a restoration. The natural teeth are then properly shaped to receive a restoration. Digital imagery of the prepared teeth is taken as shown in FIG. 12 such that the shape and location of the teeth 40 are recorded in the three dimensional digital imagery. The prepared provisional template 10 is then placed on the teeth as shown in FIG. 13. The provisional template 10 can be manually moved by the dentist or auxiliary personnel by proper manipulation from the operator's fingers 74. As illustrated in FIG. 14, the provisional template 10 may be vertically and horizontally positioned at an angle 75 compared to the natural tooth plane indicated as 73. The template angle 75 may be set at an angle that provides the best appearance for the restoration. The best vertical, i.e. reveal and horizontal facial planes may be visually determined by taking into account many vertical and horizontal planes of the face, i.e. the top of the head, the forehead, the eyebrow plane, the plane of the eyes, the plane of the cheek bones and the upper and lower lip angles and lower jaw. The best vertical plane can be decided upon based on lip position at rest and high-or-low smile lines. At rest, it is desirable to see 1-2 mm of incisal length of the maxillary central. Modifications (additions and/or subtractions) may be made to the provisional template as needed.

Figure 15:
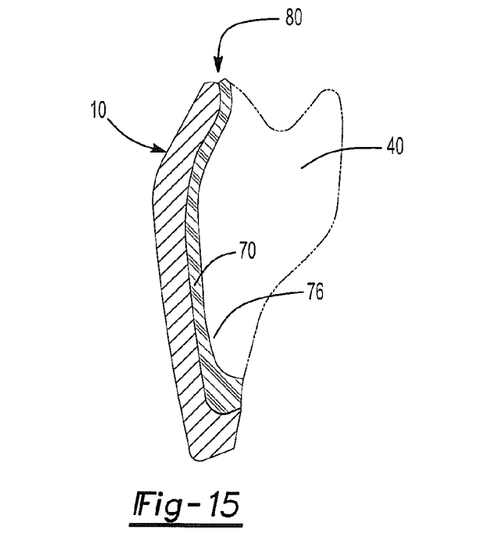
FIG. 15 is a cross-sectional view taken along lines 15-15 shown in FIG. 13 illustrating the demonstration dental template attached with a temporary adhesive to the natural teeth.

As clearly shown in FIG. 15, the provisional template 10 covers the exterior front surface 76 of the natural teeth 40 to the incisal biting edge of the front surface of the teeth 40. A thin layer of adhesive 70 provides the necessary adhesive of the template 10 to the teeth 40. Once the dentist sets the planes, makes necessary modifications and confers with the patient that the provisional template 10 is at the best vertical and horizontal facial planes. Digital imaging is then taken in the set angle and vertical location as shown in FIG. 14 with the camera head 72. Digital imagery is taken directly from the front to best record the desired plane of occlusion and desired incisal length of the restoration. Other digital imagery may be taken to relate the template to natural teeth. The three dimensional digital imagery showing the incisal length and desired occlusal plane are then shipped off i.e. electronically or by other methods, to the lab for manufacturing the final restoration. The three dimensional digital imagery records the prepared natural teeth that individually correspond to the natural teeth 40 and in series lie in the tooth plane 73. The digital imagery of the demonstration dental template also records the desired facial angle 75 set by the provisional template 10 independent from tooth plane 73. This desired facial angle is communicated to the laboratory technician to manufacture the permanent dental restoration or other permanent overlay or prosthesis with the desired cant and incisal length. The provisional template 10 may be used as a temporary until the permanent restoration is made and fitted and can also be imaged to confirm and communicate desired plane of occlusion and incisal length desired.

The provisional template may be completely set and may require relining to adhere to the teeth. Alternatively, the provisional template may be pliable and not set. The unset embodiment allows for manipulation prior to final set a well as after final set to allow changes in appearance and function which can be communicated to the patient and laboratory for the desired final restoration. The unset embodiment may be set with ultraviolet light for curing.

In this fashion, all information as to the tooth plane and facial plane are easily communicated to the technician of the restoration with a demonstration dental template and or provisional template. The demonstration dental template 10 has multiple purposes. Firstly, it demonstrates the appearance of a dental restoration. Secondly, it helps visually to determine the appropriate facial plane in which the restoration should follow. Thirdly, the digital imagery communicates to the lab the appropriate desired facial angle of the overlay relative to the tooth plane to establish vertical, i.e. reveal and horizontal tooth planes. The best aesthetic results can now also be accomplished all through digital imagery.

Alternatively for prepared teeth and where the patient needs a full coverage restoration, the patient can be fitted with a temporary full crowns 110 available for more difficult situations, as shown in FIGS. 16-20. The full crown 110 may be sized, shaped and colored to match template 10 so the patient may have the new desired look and shape of new teeth while waiting for the manufacture and installation of the permanent porcelain restoration.

Figure 16:
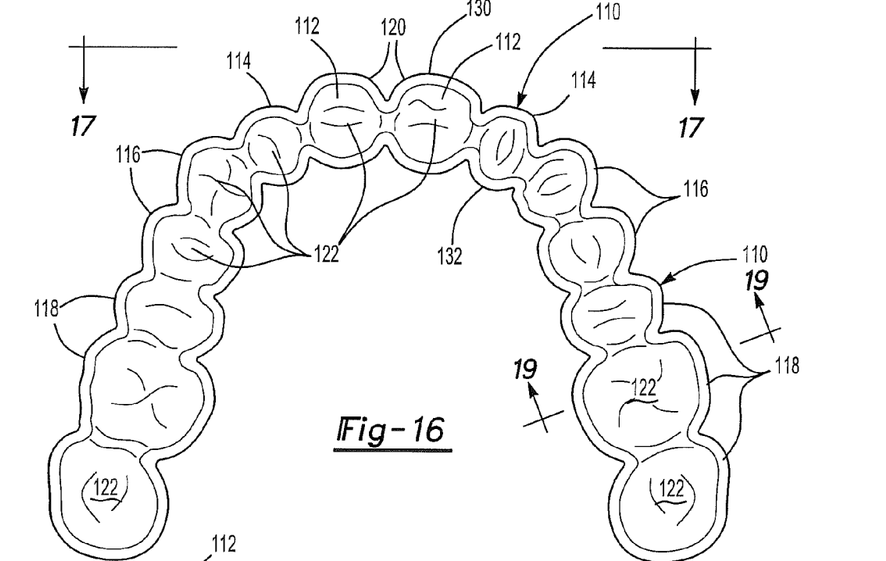
FIG. 16 is a top plan view of a temporary or provisional restoration to illustrate the internal cavities 122 according to an embodiment of the invention.

The temporary restoration 110 as shown in FIG. 16 includes a plurality of simulated teeth sections, for example simulated incisor sections 112, simulated cuspid sections 114, simulated bicuspid sections 116 and simulated molar sections 118. The overlay 110 has each section 112, 114, 116, and 118 with its outer front surface 120 simulating natural teeth as shown and demonstrated by the template 10. As such, the template 10 and temporary restoration 110 can be packaged and sold together as a kit. The size, shape and color of each template 10 is matched by a corresponding temporary restoration 110 as shown by comparison FIG. 17 with FIG. 1.

Figures 17, 18, 19, 20:
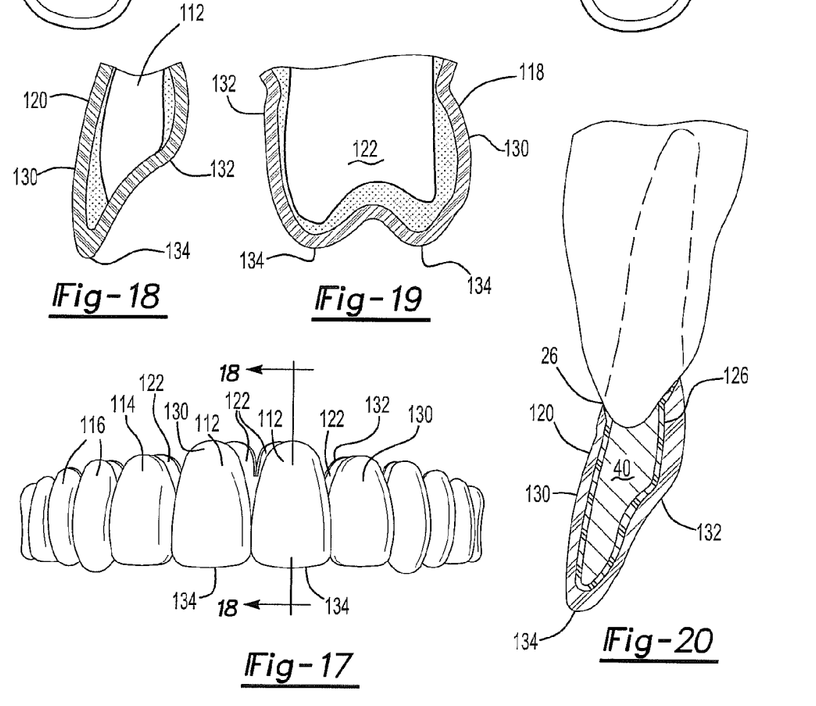
FIG. 17 is a front elevational view of the temporary or provisional restoration shown in FIG. 16.
FIG. 18 is a cross-sectional view taken along lines 18-18 shown in FIG. 17.
FIG. 19 is a cross-sectional view taken along lines 19-19 shown in FIG. 16.
FIG. 20 is a view similar to FIG. 18 showing the temporary or provisional restoration installed and bonded to a patient's prepared teeth.

The temporary restoration 110 also has each section 112, 114, 116 and 118 with a front exterior wall 130, rear wall 132 and interior cavities 122 there between as shown in FIGS. 18 and 19 sized to receive the prepared natural teeth 40 of the patient. When the temporary restoration 110 is installed, it may be modified and/or relined with suitable curable material 128 to fill any space between the overlay 110 and the prepared natural teeth 40 and cured in place. The front and rear walls 130, 132 are joined at the distal end to form a properly shaped biting edge 134 below cavity 122. The biting edge 134 is shaped to correctly correspond to the respective incisor, cuspid, bicuspid or molar section 112, 114, 116, 118. The overlay 110 may be made from a suitably temporary crown or overlay material for example, methyl methacrylate, an acrylic resin or duracetyl material. As shown in FIG. 20, the interior cavity 127 can be relined and filled with suitable curing and bonding material 126 to intimately fit the temporary restoration 110 to the prepared patient's teeth 40. In another form of the invention, the provisional would be provided in an uncured state which would allow intimate adaptation of the resin or similar material through manipulation prior to the final cure.

The overlay 110 is strong enough to provide one or more sections to act as a temporary restoration to fill any gap in-between the prepared teeth 40. While the illustrated restoration 110 is made to cover both the front and rear side of a prepared tooth, there may be occasions when the restoration 110 may only have the front side of the natural teeth. In these situations, the temporary restoration 110 may be shaped identically as the demonstration dental template 10 shown in FIGS. 1-4 to be adhered only onto the prepared front of the natural teeth. This front temporary restoration 110 is made from the same suitably temporary material, for example methyl-methacrylate, an acrylic resin, or duracetyl.

For either situation, the patient has a temporary that provides for a cosmetic improvement over the natural teeth 40 that closely matches the original demonstration dental template in size, appearance and color while waiting for the permanent veneer to be manufactured or such that can be modified slightly to meet patients aesthetic desires and functional needs of the case.

Other variations and modifications are possible without departing from the scope and spirit of the present invention as defined by the appended claims.

The embodiments in which an exclusive property or privilege is claimed are defined as follows:

1. A method for setting a desired horizontal plane of occusion and the incisal length of a permanent dental restoration; said method comprising the steps of:
    temporarily adhering a demonstration dental template that is pre-cured and pre-set at a desired position to overlay in front of the teeth of a patient at a desired plane of occusion and at a desired incisal length to provide an unobstructed view of the demonstration dental template to said patient;
    taking digital imagery of said demonstration dental template at said desired position to record said desired plane of occlusion and said desired incisal length;
    removing said demonstration dental template from said teeth;
    then preparing natural teeth for the installation of a permanent restoration;
    taking three dimensional digital imagery of said prepared teeth; and
    correlating said digital imagery of said prepared teeth with said digital imagery of said demonstration dental template for use in manufacturing said permanent restoration.

2. A method as defined in claim 1 further comprising:
    said step of adhering said demonstration dental template being to unprepared natural teeth before the preparing of the natural teeth for the installation of permanent restoration.

3. A method as defined in claim 2 further comprising:
    filling a cavity in a temporary restoration which is previously set and hardened and has simulated teeth with a curing agent and placing the temporary overlay with the prepared natural teeth; and
    curing the curing agent to temporarily bond the temporary restoration with said prepared natural teeth.

4. A method as defined in claim 2 wherein said temporary restoration is pliable and not set and is set and cured after being installed onto said prepared natural teeth.

5. A method as defined in claim 1 further comprising:
    said step of preparing said natural teeth being before temporarily adhering said demonstration dental template whereby said demonstration dental template is temporarily adhered to said natural teeth that are already prepared for a permanent restoration.

6. A method as defined in claim 5 further comprising:
    filling a cavity in a temporary restoration which has simulated teeth with a curing agent and placing the temporary restoration with the prepared natural teeth; and
    curing the curing agent to temporarily bond the temporary restoration with said prepared natural teeth.

7. A method as defined in claim 5 wherein said temporary restoration is pliable and not set and is set and cured after being installed onto said prepared natural teeth.

8. A method as defined in claim 1 further comprising:
    filling a cavity in a temporary overlay which is previously set and hardened and has simulated teeth with a curing agent and placing the temporary overlay with the prepared natural teeth; and
    curing the curing agent to temporarily bond the temporary restoration with said prepared natural teeth.

9. A method as defined in claim 1 wherein said temporary restoration is pliable and not set and is set and cured after being installed onto said prepared natural teeth.

* * * * *